(12) United States Patent
Mori

(10) Patent No.: US 6,908,945 B2
(45) Date of Patent: Jun. 21, 2005

(54) ESTER COMPOUND AND ITS USE

(75) Inventor: Tatsuya Mori, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 104 days.

(21) Appl. No.: 10/410,354

(22) Filed: Apr. 10, 2003

(65) Prior Publication Data

US 2003/0195119 A1 Oct. 16, 2003

(30) Foreign Application Priority Data

Apr. 12, 2002 (JP) .......................... 2002-110348

(51) Int. Cl.[7] .......................... A01N 37/34; A01N 53/02; A01N 53/06; C07C 255/39; C07C 255/31
(52) U.S. Cl. .................. 514/521; 514/531; 558/407; 560/124; 504/309
(58) Field of Search ................ 514/521, 531; 558/407; 560/124; 504/309

(56) References Cited

U.S. PATENT DOCUMENTS 5,135,951 A    8/1992  Babin et al.
6,294,576 B1   9/2001  Mori
2005/0004389 A1 * 1/2005  Mori ..................... 558/407

FOREIGN PATENT DOCUMENTS

IN   152306 Prov    6/1980
WO   WO 99/32426 A1  7/1999

* cited by examiner

*Primary Examiner*—John Pak
(74) *Attorney, Agent, or Firm*—Birch, Stewart, Kolasch & Birch, LLP

(57) ABSTRACT

A cyclopropanecarboxylic acid ester compound of formula (1):

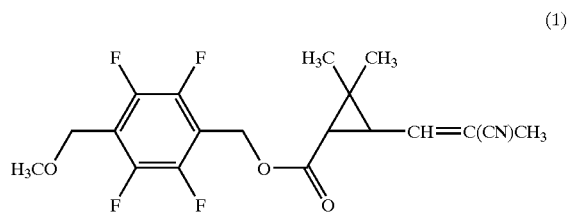

(1)

has an excellent pesticidal efficacy, and a pesticidal composition comprising it as an active ingredient is useful for controlling pests.

3 Claims, No Drawings

ESTER COMPOUND AND ITS USE

FIELD OF THE INVENTION

The present invention relates to an ester compound and its use for pesticide.

BACKGROUND ARTS

Many pyrethroid compounds are known and developed for pesticidal use. An ester of 4-methoxymethyl-2,3,5,6-tetrafluorobenzyl alcohol is described in WO 99/32426 and 3-phenoxybenzyl 3-(2-cyano-1-propenyl)-2,2-dimethylcyclopropanecarboxylate is described in Indian Patent No. 152306.

SUMMARY OF THE INVENTION

The present invention provides a compound having an excellent pesticidal activity.

Namely, the present invention provides an ester compound given by formula (1):

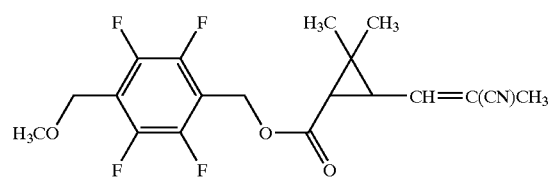

(1)

(hereinafter, referred to as the present compound), a pesticidal composition which comprises the ester compound as an active ingredient and an inert carrier, and a method for controlling pests which comprises applying an effective amount of the ester compound to the pests or a place the pests inhabit.

DETAILED DESCRIPTION OF THE INVENTION

The ester compound has the isomers originated from two asymmetric carbon atoms on the cyclopropane ring and the isomers originated from the double bond. The present invention includes, any active isomers and compounds containing the isomers at any ratio.

Examples of the active isomers as below and they are preferably used for controlling pests.
The compound of formula (1):

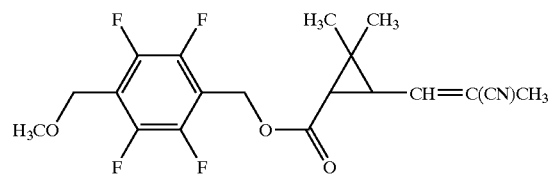

(1)

wherein the absolute configuration of 1-position on the cyclopropane ring is R-configuration;
The compound of formula (1) wherein the configuration of the substituent on 1-position of the cyclopropane ring and the substituent on 3-position of the cyclopropane ring is trans configuration;
The compound of formula (1) wherein the configuration of the substituent on 1-position of the cyclopropane ring and the substituent on 3-position of the cyclopropane ring is cis configuration;
The compound of formula (1) wherein the configuration of the double bond existing on the substituent on 3-position of the cyclopropane ring is Z-configuration;
The compound of formula (1) wherein the absolute configuration of 1-position on the cyclopropane ring is R-configuration and the configuration of the substituent on 1-position of the cyclopropane ring and the substituent on 3-position of the cyclopropane ring is trans configuration;
The compound of formula (1) wherein the absolute configuration of 1-position on the cyclopropane ring is R-configuration and the configuration of the substituent on 1-position of the cyclopropane ring and the substituent on 3-position of the cyclopropane ring is cis configuration;
The compound of formula (1) wherein the absolute configuration of 1-position on the cyclopropane ring is R-configuration, the configuration of the substituent on 1-position of the cyclopropane ring and the substituent on 3-position of the cyclopropane ring is trans configuration and the configuration of the double bond existing on the substituent on 3-position of the cyclopropane ring is Z-configuration;
The compound of formula (1) wherein the absolute configuration of 1-position on the cyclopropane ring is R-configuration, the configuration of the substituent on 1-position of the cyclopropane ring and the substituent on 3-position of the cyclopropane ring is cis configuration and the configuration of the double bond existing on the substituent on 3-position of the cyclopropane ring is Z-configuration;
The compound of formula (1) wherein the isomer, which is the absolute configuration of 1-position on the cyclopropane ring is R-configuration and the configuration of the substituent on 1-position of the cyclopropane ring and the substituent on 3-position of the cyclopropane ring is trans configuration, is rich;
The compound of formula (1) containing 80% or more of the isomer, which is the absolute configuration of 1-position on the cyclopropane ring is R-configuration and the configuration of the substituent on 1-position of the cyclopropane ring and the substituent on 3-position of the cyclopropane ring is trans configuration; and
The compound of formula (1) containing 90% or more of the isomer, which is the absolute configuration of 1-position on the cyclopropane ring is R-configuration and the configuration of the substituent on 1-position of the cyclopropane ring and the substituent on 3-position of the cyclopropane ring is trans configuration;

The present compound can be produced, for example, by making an aldehyde compound given by formula (2):

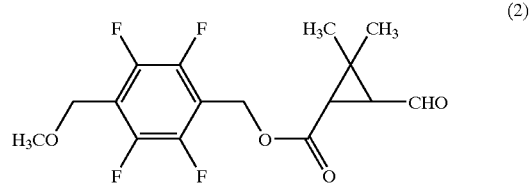

(2)

react with diethyl (1-cyanoethyl)phosphonate given by formula (3):

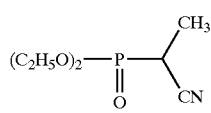

(3)

The reaction is usually carried out in a solvent in the presence of a base.

Examples of the solvent used for the reaction include hydrocarbons such as hexane, heptane, octane and toluene; ethers such as diethyl ether and tetrahydrofuran; and mixtures thereof.

Examples of the base used for the reaction include alkali alkoxides such as sodium methoxide and potassium t-butoxide; alkali hydrides such as sodium hydride and potassium hydride; and alkali amides such as sodium bistrimethylsilylamide, lithium bistrimethylsilylamide and lithium bisisopropylamide.

The amount of diethyl (1-cyanoethyl)phosphonate given by formula (3) used for the reaction is usually 0.8 to 1.5 mols and the amount of the base is 0.8 to 1.5 mols based on 1 mol of the aldehyde compound given by formula (2), respectively.

The reaction time is usually within the range of momentary to 72 hours and the reaction temperature is usually within −80 to 80° C.

After the reaction has been completed, work-up procedures are performed so that the reaction mixture is poured into water and extracted with an organic solvent and the obtained organic layer is dried and concentrated. The isolated compound of the present invention may be further purified by chromatography and the like.

The aldehyde compound given by formula (2) can be prepared by decomposing the compound given by formula (4):

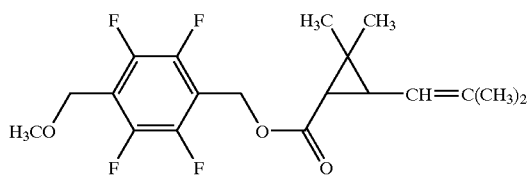

(4)

with ozone, or making the compound given by formula (4) react with osmium tetraoxide-sodium metaperiodate.

The present compound can also be produced by making 4-methoxymethyl-2,3,5,6-tetrafluorobenzyl alcohol given by formula (5):

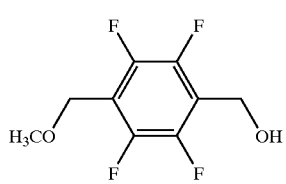

(5)

react with a carboxylic acid given by formula (6):

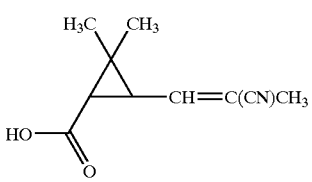

(6)

or its reactive derivative.

The reactive derivative include acid halide (e.g. acid chloride, acid bromide), acid anhydride and so on.

The compound given by formula (4) is described in U.S. Pat. No. 6,294,576, and it can be produced by the method described in the publication.

The 4-methoxymethyl-2,3,5,6-tetrafluorobenzyl alcohol given by formula (5) is a compound described in U.S. Pat. No. 4,370,346, and it can be produced by the method described in the publication.

The carboxylic acid compound given by formula (6) can be derived from its tert-butyl ester by hydrolysis. The tert-butyl ester is a compound described in Agr. Biol. Chem., 34, 1119 (1970) and can be prepared from tert-butyl 3-formyl-2,2-dimethylcyclopropanecarboxylate and diethyl (1-cyanoethyl)phosphonate given by formula (3). In the preparation, tertbutyl 3-formyl-2,2-dimethylcyclopropanecarboxylate can be obtained by ozonolysis of tert-butyl chrysanthemate. And also the carboxylic acid compound given by formula (6) is a compound described in Indian Patent No. 152306, and it can be produced by the method described in the publication.

Examples of the pests controlled by the present compound include arthropods such as insects and acarina. Typical examples are as follows.

*Lepidoptera:*

Pyralidae such as *Chilo suppressalis* (rice stem borer), *Cnaphalocrocis medinalis* (rice leafroller) and *Plodia interpunctella* (Indian meal moth); Noctuidae such as *Spodoptera litura* (tobacco cutworm), *Pseudaletia separata* (rice armyworm) and *Mamestra brassicae* (cabbage armyworm); Pieridae such as *Pieris rapae crucivora* (common cabbageworm); Tortricidae such as *Adoxophyes* spp.; Carposinidae; Lyonetiidae; Lymantriidae; Plusiinae; *Agrotis* spp. such as *Agrotis segetum* (turnip cutworm) and *Agrotis ipsilon* (black cutworm); *Helicoverpa* spp.; *Heliotis* spp.; *Plutella xylostella* (diamondback moth); *Parnara guttata* (rice skipper); *Tinea pellionella* (casemaking clothes moth); *Tineola bisselliella* (webbing clothes moth); and so on;

*Diptera:*

*Culex* spp. such as *Culex pipiens pallens* (common mosquito) and *Culex tritaeniorhynchus*; *Aedes* spp. such as *Aedes aegypti* and *Aedes albopictus*; *Anopheles* spp. such as *Anopheles sinensis*; Chironomidae (midges); Muscidae such as *Musca domestica* (housefly), *Muscina stabulans* (false stablefly) and *Fannia canicularis* (little housefly); Calliphoridae; Sarcophagidae; Anthomyiidae such as *Delia platura* (seedcorn maggot) and *Delia antiqua* (onion maggot); Tephritidae (fluit flies); Drosophilidae; Psychodidae (moth flies); Phoridae; Tabanidae; Simuliidae (black flies); Stomoxyidae; Ceratopogonidae (biting midges); and so on;

*Dictyoptera:*

*Blattella germanica* (German cockroach), *Periplaneta fuliginosa* (smokybrown cockroach), *Periplaneta americana* (American cockroach), *Periplaneta brunnea* (brown cockroach), *Blatta orientalis* (oriental cockroach) and so on;

Hymenoptera:
Formicidae (ants); Vespidae (hornets); Bethylidae; Tenthredinidae (sawflies) such as *Athalis rosae ruficornis* (cabbage sawfly); and so on;
Siphonaptera:
*Ctenocephalides canis* (dog flea), *Ctenocephalides felis* (cat flea), *Pulex irritans* and so on;
Anoplura:
*Pediculus humanus humanus* (body louse), *Pthirus pubis* (crab louse), *Pediculus capitis* (head louse), *Pediculus corporis* and so on;
Isoptera:
*Reticulitermes speratus; Coptotermes formosanus*; and so on;
Hemiptera:
Delphacidae (planthoppers) such as *Laodelphax striatellus* (small brown planthopper), *Nilaparvata lugens* (brown planthopper) and *Sogatella furcifere* (white backed rice planthopper); leafhoppers such as *Nephotettix cincticeps, Nephotettix virescens*; Aphididae (aphids); plant bugs; Aleyrodidae (whiteflies); scales; Tingidae (lace bugs); Psyllidae; and so on;
Coleoptera (beetles):
*Attagenus unicolor japonicus* (black carpet beetle) and *Authrenus verbasci* (varied carpet beetle); corn rootworms such as *Diabrotica virgifera* (western corn rootworm) and *Diabrotica undecimpunctata howardi* (southern corn rootworm); Scarabaeidae such as *Anomala cuprea* (cupreous chafer) and *Anomala rufocuprea* (soybeen beatle); weevils such as *Sitophilus zeamais* (maize weevil), *Lissorhoptrus oryzophilus* (ricewater weevil), ball weevil and *Callosobruchus chinensis* (adzuki bean weevil); Tenebrionidae (darkling beetles) such as *Tenebrio molitor* (yellow mealworm) and *Tribolium castaneum* (red flour beetle); Chrysomelidae (leaf beetles) such as *Oulema oryzae* (rice leaf beetle), *Phyllotreta striolata* (striped flea beetle) and *Aulacophora femoralis* (cucurbit leaf beetle); Anobiidae; Epilachna spp. such as *Epilachna vigintioctopunctata* (twenty-eight- spotted ladybird); Lyctidae (powderpost beetles); Bostrychidae (false powderpost beetles); Cerambycidae; *Paederus fuscipes* (robe beetle); and so on;
Thysanoptera:
*Thrips palmi, Flankliniella occidentalis* (western flower thrips), *Thrips hawaiiensis* (flower thrips) and so on;
Orthoptera:
Gryllotalpidae (mole crickets); Acrididae (grasshoppers); and so on;
Acarina:
Dermanyssidae such as *Dermatophagoides farinae* (American house dust mite) and *Dermatophagoides pteronyssinus*; Acaridae such as *Tyrophagus putrescentiae* (mold mite) and *Aleuroglyphus ovatus*; Glycyphagidae such as *Glycyphagus privatus, Glycyphagus domesticus* and *Glycyphagus destructor*; Cheyletidae such as *Chelacaropsis malaccensis* and *Cheyletus fortis*; Tarsonemidae; Chortoglyphus spp.; Haplochthonius spp.; Tetranychidae such as *Tetranychus urticae* (carmine spider mite), *Tetranychus kanzawai* (Kanzawa spider mite), *Panonychus citri* (citrus red mite) and *Panonychus ulmi* (European red mite); Ixodidae such as *Haemaphysalis longiconis*; and so on.

The pesticidal composition of the present invention is comprised the present compound and an inert carrier, it is formulated in general.

Examples of the formulations include oil solutions, emulsifiable concentrates, wettable powders, flowable formulations (e.g. aqueous suspension, aqueous emulsion), dusts, granules, aerosols, volatile formulations by heating (e.g. mosquito-coil, mosquito-mat for electric heating, volatile formulations with absorptive wick for heating), heating fumigants (e.g. self-burning type fumigants, chemical reaction type fumigant, porous ceramic plate fumigant), non-heating volatile formulations (e.g. resin volatile formulations, impregnated paper volatile formulations), smoking formulations (e.g. fogging), ULV formulations and poisonous baits.

The formulation methods are, for example, as follows.
(1) A method of mixing the present compound with a solid carrier, liquid carrier, gaseous carrier, bait or the like, optionally adding auxiliaries for formulation such as surfactants and the like, and formulating the mixture.
(2) A method of impregnating a base material containing no active ingredients with the present compound.
(3) A method of mixing the present compound with a base material and forming the mixture.

The content of the present compound depends on the type of formulations, but these formulations usually contain 0.001 to 95% by weight of the present compound.

Examples of the carrier to be used for the formulation include solid carriers such as clays (e.g. kaolin clay, diatomaceous earth, synthetic hydrated silicon oxide, bentonite, Fubasami clay, acid clay), talc and the like, ceramics, other inorganic minerals (e.g. sericite, quartz, sulfur, active carbon, calcium carbonate, hydrated silicon oxide, montmorillonite) and chemical fertilizers (e.g. ammonium sulfate, ammonium phosphate, ammonium nitrate, urea, ammonium chloride); liquid carriers such as water, alcohols (e.g. methanol, ethanol), ketones (e.g. acetone, methyl ethyl ketone), aromatic hydrocarbons (e.g. benzene, toluene, xylene, ethylbenzene, methylnapbthalene, phenylxylylethane), aliphatic hydrocarbons (e.g. hexane, cyclohexane, kerosene, gas oil), esters (ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (dichloromethane, trichloroethane, carbon tetrachloride), dimethyl sulfoxide, vegetable oils (e.g. soybean oil, cottonseed oil); and gaseous carriers such as flon gas, butane gas, LPG (liquefied petroleum gas), dimethyl ether and carbon dioxide.

Examples of the surfactant include alkyl sulfates, alkylsulfonates, alkylarylsulfonates, alkyl aryl ethers, polyoxyethylenealkyl aryl ethers, polyethylene glycol ethers, polyhydric alcohol esters and sugar alcohol derivatives.

Examples of the other auxiliaries for formulation include sticking agents, dispersing agents and stabilizers, typically casein, gelatin, polysaccharides (e.g. starch, gum arabic, cellulose derivatives, alginic acid), lignin derivatives, bentonite and synthetic water-soluble polymers (e.g. polyvinyl alcohol, polyvinylpyrrolidone), polyacrylic acid, BHT (2,6-di-tert-butyl-4-methyphenol) and BHA (mixture of 2-tert-butyl-4-methoxyphenol and 3- tert-butyl-4-methoxyphenol).

An example of the base material of the mosquito-coil is a mixture of raw plant powder such as wood powder and Pyrethrum marc and a binding agent like Tabu powder (powder of *Machilus thunbergii*), starch or gluten.

An example of the base material of the mosquito-mat for electric heating is a plate of compacted fibrils of cotton linters or a mixture of pulp and cotton linters.

The base material of the self-burning type fumigant includes, for example, exothermic agents (e.g. nitrates, nitrites, guanidine salts, potassium chlorate, nitrocellulose, ethylcellulose, wood powder), pyrolytic stimulating agents (e.g. alkali metal salts, alkaline earth metal salts, dichromates and chromates), oxygen sources (e.g. potassium nitrate), combustion assistants (e.g. melanin, wheat starch), bulk fillers (e.g. diatomaceous earth) and binding agents (e.g. synthetic glue).

The base material of the chemical reaction type fumigant includes, for example, an exothermic agents (e.g. alkali metal sulfides, polysulfides, hydrogensufides, calcium oxide), catalytic agents (e.g. carbonaneous substances, iron carbide and activated clay), organic foaming agents (e.g. azodicarbonamide, benzenesulfonylhydrazide, dinitrosopentamethylene tetramine, polystyrene, polyurethane) and fillers (e.g. natural or synthetic fibers).

Examples of the base material of the non-heating volatile formulation include thermoplastic resins and paper (e.g. filter paper, Japanese paper).

The base material of the poisonous bait includes bait components (e.g. grain powder, vegetable oil, sugar, crystalline cellulose), antioxidants (e.g. dibutylhydroxytoluene, nordihydroguaiaretic acid), preservatives (e.g. dehydroacetic acid), substances for preventing erroneous eating from children and pets (e.g. red pepper powder), pest-attractant flavors (e.g. cheese flavor, onion flavor, peanut oil).

The method for controlling pests of the present invention is usually carried out by applying the pesticidal composition of the present invention to the pests or a place where the pests inhabit.

The application methods of the pesticidal composition of the present invention are, for example, given below. The methods are suitably selected according to the type of the pesticidal composition or application places.

(1) A method applying the pesticidal composition of the present invention as it is to pests or a place where the pests inhabit.
(2) A method diluting the pesticidal composition of the present invention with a solvent such as water, and then spraying it to pests or a place where the pests inhabit.

In that case, the pesticidal composition of the present invention formulated to emulsifiable concentrates, wettable powders, flowable formulations, microcapsule formulations and so on is diluted to make the concentration of the present compound to 0.1 to 10000 ppm.

(3) A method volatilizing an active ingredient by heating the pesticidal composition of the present invention at a place where pests inhabit.

In that case, the dosage and concentration of the present compound are decided according to type of the pesticidal composition of the present invention, time, place and method of the application, kind of the pests, damage and so on.

The pesticidal composition of the present invention can be used simultaneously with the other insecticide, nematocide, soil-pest controlling agent, fungicide, herbicide, plant growth regulator, repellent, synergist, fertilizer or soil conditioner under pre-mixed conditions or non-mixed conditions.

Examples of the active ingredients of the insecticide and acaricide include organophosphorus compounds such as fenitrothion, fenthion, diazinon, chlorpyrifos, acephate, methidathion, disulfoton, DDVP, sulprofos, cyanophos, dioxabenzofos, dimethoate, phenthoate, malathion, trichlorfon, azinphos-methyl, monocrotophos and ethion; carbamate compounds such as BPMC, benfracarb, propoxur, carbosulfan, carbaryl, methomyl, ethiofencarb, aldicarb, oxamyl and fenothiocarb; pyrethroid compounds such as etofenprox, fenvalerate, esfenvalerate, fenpropathrin, cypermethrin, permethrin, cyhalothrin, deltamethrin, cycloprothrin, fluvalinate, bifenthrin, 2-methyl-2-(4-bromodifluoromethoxyphenyl)propyl 3-phenoxybenzyl ether, tralomethrin, silafluofen, d-phenothrin, cyphenothrin, d-resmethrin, acrinathrin, cyfluthrin, tefluthrin, transfluthrin, tetramethrin, allethrin, d-furamethrin, prallethrin, empenthrin and 5-(2-propynyl)furfuryl 2,2,3,3-tetramethylcyclopropanecarboxylate; nitroimidazolidine derivatives; N-cyanoamidine derivatives such as acetamiprid; chlorinated hydrocarbons such as endosulfan, γ-BHC and 1,1-bis(chlorophenyl)-2,2,2-trichloroethanol; benzoylphenylurea compounds such as chlorfluazuron, teflubenzuron and flufenoxuron; phenylpyrazole compounds; metoxadiazon; bromopropylate; tetradifon; chinomethionat; pyridaben; fenpyroximate; diafenthiuron; tebufenpyrad; polynactins complex such as tetranactin, dinactin and trinactin; pyrimidifen; milbemectin; abamectin; ivermectin; and azadirachtin.

Examples of the repellent include 3,4-caranediol, N,N-diethyl-m-toluamide, 1-methylpropyl 2-(2-hydroxyethyl)-1-piperidinecarboxylate, p-menthan-3,8-diol, botanical essential oils (e.g. hyssop oil).

Examples of the synergist include bis(2,3,3,3-tetrachloropropyl) ether (S-421), N-(2-ethylhexyl)bicyclo[2.2.1]hept-5-ene-2,3-dicarboximide (MGK-264) and α-[2-(2-butoxyethoxy)ethoxy]-4,5-methylenedioxy-2-propyltoluene (piperonyl butoxide).

EXAMPLES

The present invention is explained by production example, formulation examples, test example and so on, and the present invention is not restricted by these examples.

At first, the production example of the present compound is given below.

Production Example

Under nitrogen atmosphere, 0.54 g of diethyl (1-cyanoethyl) phosphonate was dissolved in 6 ml of tetrahydrofuran and 2.8 ml of a tetrahydrofuran solution of sodium bis(trimethylsilyl)amide (1 mol/l) were added thereto at about 0° C. The mixture was stirred for 30 minutes and 2 ml of a tetrahydrofuran solution containing 1.0 g of 4-methoxymethyl-2,3,5,6-tetrafluorobenzyl 3-formyl-2,2-dimethylcyclopropanecarboxylate given by formula (7):

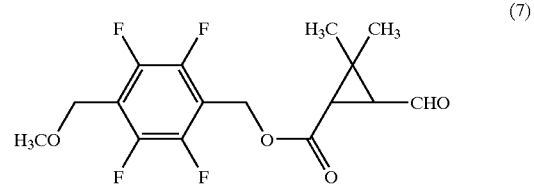

(7)

(prepared by the method described as reference production example 1 below) was added thereto and stirred for 3 hours at room temperature. After that, the reaction mixture was poured into about 20 ml of 1% hydrochloric acid and extracted with 100 ml of ethyl acetate. The organic layer was washed with saturated aqueous sodium hydrogencarbonate solution and saturated brine, subsequently, dried over anhydrous sodium sulfate and concentrated under reduced pressure. The obtained residue was subjected to silica gel column chromatography to give 0.76 g of 4-methoxymethy-2,3,5,6-tetrafluorobenzyl 3-(2-cyano-1-propenyl)-2,2-dimethylcyclopropanecarboxylate given by formula (8):

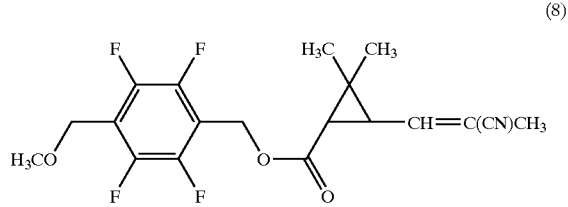

(8)

(isomers ratio based on the double bond: Z/E=about 2/1).

$^1$H-NMR (CDCl$_3$, TMS) δ (ppm): 1.21 (s, 3H, Z+E forms), 1.32 (s, 3H, Z+E forms), 1.73 (m, 1H, Z+E forms), 1.96 (s, 3H, Z+E forms), 2.20 (m, 1/3H, E form), 2.47 (m, 2/3H, Z form), 3.41 (s, 3H, Z+E forms), 4.59 (s, 2H, Z+E forms), 5.26 (s, 2H, Z+E forms), 5.78 (m, 2/3H, Z form), 6.01 (m, 1/3H, E form)

Reference Production Example 1

In 10 ml of tetrahydrofuran, 1.0 g of 4-methoxymethy-2,3,5,6-tetrafluorobenzyl alcohol and 0.42 g of pyridine were dissolved, 0.9 g of 3-(2-methyl-1-propenyl)-2,2-dimethylcyclopropanecarboxylic chloride {stereoisomers ratio (1R)-trans:(1R)-cis:(1S)-trans:(1S)-cis= 93.9:2.5:3.5:0.1} was added thereto and stirred for 8 hours at room temperature. After that, the reaction mixture was poured into about 50 ml of ice-water and extracted with 80 ml of ethyl acetate twice. The combined organic layer was washed with saturated brine, dried over anhydrous sodium sulfate and concentrated under reduced pressure. The obtained residue was subjected to silica gel column chromatography to give 1.4 g of 4-methoxymethy-2,3,5,6-tetrafluorobenzyl 3-(2-methyl-1-propenyl)-2,2-dimethylcyclopropane-carboxylate.

$^1$H-NMR (CDCl$_3$, TMS) δ (ppm): 1.13 (s, 3H), 1.26 (s, 3H), 1.38 (d, 1H), 1.69 (brs, 6H), 2.10 (dd, 1H), 3.40 (s, 3H), 4.59 (s, 2H), 4.87 (d, 1H), 5.24 (dd, 2H)

To a mixture of 25 ml of tetrahydrofuran and 150 ml of 1,4-dioxane, 15.4 g of 4-methoxymethy-2,3,5,6-tetrafluorobenzyl 3-(2-methyl-1-propenyl)-2,2-dimethylcyclopropanecarboxylate (prepared by the method described above) were dissolved and 1.0 g of osmium tetraoxide was added thereto at room temperature. Further, 50 ml of water containing 24.0 g of sodium metaperiodate were added thereto and refluxed for 2 hours under heating. After that, the reaction mixture was poured into about 200 ml of water and extracted with 200 ml of ethyl acetate twice. The combined organic layer was washed with 1% aqueous sodium thiosulfate solution, saturated aqueous sodium hydrogencarbonate solution and saturated brine, subsequently, dried over anhydrous sodium sulfate and concentrated under reduced pressure. The obtained residue was subjected to silica gel column chromatography to give 10.4 g of 4-methoxymethy-2,3,5,6-tetrafluorobenzyl 3-formyl-2,2-dimethylcyclopropanecarboxylate.

$^1$H-NMR (CDCl$_3$, TMS) δ (ppm): 1.30 (s, 3H), 1.36 (s, 3H), 2.47 (m, 2H), 3.41 (s, 3H), 4.59 (s, 2H), 5.26 (s, 2H), 9.59 (s, 1H)

Formulation examples are given below. Part(s) means part(s) by weight.

Formulation Example 1

Twenty parts of the present compound are dissolved in 65 parts of xylene. Fifteen parts of Sorpol 3005X (registered trademark of Toho Chemical) are added thereto, stirred and mixed well to give emulsifiable concentrate.

Formulation Example 2

Five parts of Sorpol 3005X are added to 40 parts of the present compound and mixed well. Thirty-two parts of Carplex #80 (synthetic hydrated silica, registered trademark of Shionogi & Co.) and 23 parts of 300-mesh distomaceous earth are added thereto and mixed well with a juice mixer to give wettable powders.

Formulation Example 3

One and a half parts of the present compound, 1 part of Tokusil GUN (synthetic hydrated silica, registered trademark of Shionogi & Co.), 2 parts of Reax 85A (sodium ligninsulfonate, manufactured by Westovaco chemicals), 30 parts of Bentonite Fuji (bentonite, manufactured by Hojun Co.) and 65.5 parts of Shokozan A clay (kaolin clay, manufactured by Shokozan Kogyosho Co.) are well pulverized and mixed. Water is added thereto, kneaded, granulated with a piston-granulator and dried to give 1.5% granules.

Formulation Example 4

A mixture of 10 parts of the present compound, 10 parts of phenylxylylethane and 0.5 part of Sumidur L-75 (tolylenediisocyanate manufactured by Sumitomo Bayer Urethane Co., Ltd.) is added to 20 parts of a 10% aqueous solution of gum arabic, and stirred with a homomixer to give an emulsion having the mean particle diameter of 20 µm. Two parts of ethylene glycol are added thereto and stirred 24 hours on a water bath of 60° C. to give a microcapsule slurry.

A thickening agent solution is prepared by dispersing 0.2 part of xanthan gum and 1.0 part of Beagum R (aluminum magnesium silicate manufactured by Sanyo Chemical Co., Ltd.) in 56.3 parts of ion-exchanged water.

Forty-two and a half (42.5) parts of the above microcapsule slurry and 57.5 parts of the above thickening agent solution are mixed to give microencapsulated formulation.

Formulation Example 5

A mixture of 10 parts of the present compound and 10 parts of phenylxylylethane is added to 20 parts of a 10% aqueous solution of polyethylene glycol and stirred with a homomixer to give an emulsion having the mean particle diameter of 3 µm.

A thickening agent solution is prepared by dispersing 0.2 part of xanthan gum and 1.0 part of Beagum R (aluminum magnesium silicate manufactured by Sanyo Chemical Co., Ltd.) in 58.8 parts of ion-exchanged water.

Forty parts of the above emulsion and 60 parts of the above thickening agent solution are mixed to give flowable formulation.

Formulation Example 6

Five parts of the present compound are mixed with 3 parts of Carplex #80 (fine powder of synthetic hydrated silicon dioxide, trademark of Shionogi & Co.), 0.3 parts of PAP (mixture of monoisopropyl phosphate and diisopropyl phosphate) and 91.7 parts of 300-mesh talc, and stirred with a juice mixer to give dusts.

Formulation Example 7

One-tenth (0.1) part of the present compound is dissolved in 10 parts of dichloromethane and mixed with 89.9 parts of deodorized kerosene to give oil solution.

Formulation Example 8

An aerosol vessel is filled with the solution obtained by dissolving 1 part of the present compound with 5 parts of dichloromethane and 34 parts of deodorized kerosene. The vessel is then equipped with a valve and 60 parts of propellant (liquefied petroleum gas) are charged through the valve into the aerosol vessel under pressure to give oil-based aerosol.

Formulation Example 9

An aerosol vessel is filled with 50 parts of water and a mixture of 0.6 part of the present compound, 5 parts of xylene, 3.4 parts of deodorized kerosene and 1 part of Atmos 300 (emulsifier, trademark of Atlas Chemical Co.). The vessel is then equipped with a valve and 40 parts of propellant (liquefied petroleum gas) is charged through the valve into the aerosol vessel under pressure to give water-based aerosol.

Formulation Example 10

A solution prepared by dissolving 0.3 g of the present compound in 20 ml of acetone is homogeneously mixed with 99.7 g of a carrier for a mosquito-coil (mixture of Tabu powder, Pyrethrum marc and wood powder at the ratio of 4:3:3). After 100 ml of water is added, the mixture is kneaded well, molded and dried to give mosquito-coil.

Formulation Example 11

Ten milliliters (10 ml) of solution is prepared by dissolving 0.8 g of the present compound and 0.4 g of piperonyl butoxide in acetone. 0.5 ml of the obtained solution is impregnated with a base material (a plate of compacted fibrils of a mixture of pulp and cotton linter: 2.5 cm×1.5 cm×0.3 cm of thichness) homogeneously to give mosquito-mat.

Formulation Example 12

Three parts of the present compound is dissolved in 97 parts of deodorized kerosene. The obtained solution is charged in a vessel of polyvinyl chloride. In the vessel is inserted a porous absorptive wick which is inorganic powder solidified with a binder and then calcined, the upper portion of which wick can be heated with a heater, to give a part of an electric heating fumigation device.

Formulation Example 13

A solution prepared by dissolving 100 mg of the present compound in an appropriate amount of acetone is impregnated with a porous ceramic plate (4.0 cm×4.0 cm×1.2 cm of thickness) to give fumigant for heating.

Formulation Example 14

A solution prepared by dissolving 100 μg of the present compound in an appropriate amount of acetone is applied onto filter paper (2.0 cm×2.0 cm×0.3 mm of thickness) and the acetone is vaporized to give volatile agent for using at room temperature.

The following test example shows that present compound is useful as an active ingredient of a pesticidal composition.

Test Example 1

A solution of 0.025 part of the present compound prepared by the production example mentioned above dissolved with 10 parts of dichloromethane was mixed with 89.9975 parts of deodorized kerosene to give a 0.025% oil solution.

Adult houseflies (5 males and 5 females) were left in a cubic chamber (70 cm at side). Seven-tenths (0.7) ml of the 0.025% oil solution of the present compound prepared above was sprayed with a spray gun at a pressure of $8.8 \times 10^4$ Pa from a small window on the side of the chamber. Then, the number of the knocked-down insects was counted at times for 10 minutes. The time for knocking down half of the tested insects was 1.0 minute.

Test Example 2

A solution of 0.00625 part of the present compound prepared by the production example mentioned above dissolved with 10 parts of dichloromethane was mixed with 89.99375 parts of deodorized kerosene to give a 0.00625% oil solution.

Adult houseflies (5 males and 5 females) were left in a cubic chamber (70 cm at side). Seven-tenths (0.7) ml of the 0.00625% oil solution of the present compound prepared above was sprayed with a spray gun at a pressure of $8.8 \times 10^4$ Pa from a small window on the side of the chamber. Then, the number of the knocked-down insects was counted at times for 10 minutes (two repetitions). The time for knocking down half of the tested insects ($KT_{50}$) was observed. The $KT_{50}$ value was 1.1 minutes.

The same test except that 4-methoxymethy-2,3,5,6-tetrafluorobenzyl (1R,trans)-3-(2-fluoro-1-propenyl)-2,2-dimethylcyclopropanecarboxylate, which is a compound of Example 12 of WO 99/32426, was used in place of the present compound was performed for reference. The $KT_{50}$ value was 5.0 minutes.

Test Example 3

A solution of 0.00625 part of the present compound (1R,cis-E) dissolved with 10 parts of dichloromethane was mixed with 89.99375 parts of deodorized kerosene to give a 0.025% oil solution.

Ten female common mosquitoes (*Culex pipiens pallens*) were left in a cubic chamber (70 cm at side). Seven-tenths (0.7) ml of the 0.00625% oil solution of the present compound prepared above was sprayed with a spray gun at a pressure of $8.8 \times 10^4$ Pa from a small window on the side of the chamber. Then, the number of the knocked-down insects was counted at times for 10 minutes. The time for knocking down half of the tested insects was 1.3 minute.

The same test except that 3-phenoxybenzyl (1R,cis)-3-((E)-2-cyano-1-propenyl)-2,2-dimethylcyclopropanecarboxylate, which is a compound described in Indian Patent No. 152306, was used in place of the present compound was performed for reference. The $KT_{50}$ value was 8.0 minutes.

What is claimed is:

1. An ester compound given by formula:

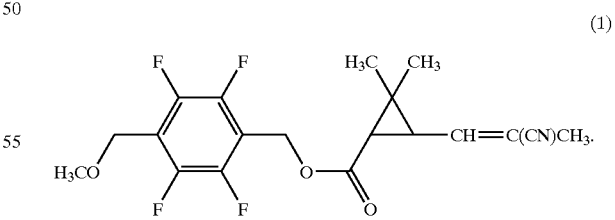

(1)

2. A pesticidal composition comprising the ester compound described in claim 1 as an active ingredient and a inert carrier.

3. A method for controlling pests comprising applying an effective amount of the ester compound described in claim 1 to the pests or a place the pests inhabit.

* * * * *